United States Patent [19]

Szabo et al.

[11] 4,366,148
[45] Dec. 28, 1982

[54] USE OF SOMATOSTATIN IN THE PREVENTION AND CURE OF VASCULAR, MEMBRANE, OR ORGAN LESIONS

[75] Inventors: Sandor Szabo, Brookline, Mass.; Klaus H. Usadel, Frankfurt am Main, Fed. Rep. of Germany

[73] Assignee: Brigham and Women's Hospital, Boston, Mass.

[21] Appl. No.: 269,734

[22] Filed: Jun. 2, 1981

[51] Int. Cl.³ .................... A61K 37/00; C07C 103/52
[52] U.S. Cl. .............................. 424/177; 260/112.5 S
[58] Field of Search ................... 424/177; 260/112.5 S

[56] References Cited

PUBLICATIONS

Computer Printout.
Schwedes et al., European Journal of Pharmacology, 44, 195 (1977).
Schwedes et al., Hormone and Metabolic Research, 11, 647 (1970).
Schwedes et al., Metabolism Supplement 1, 27, 1377 (1978).

Primary Examiner—Delbert R. Phillips
Attorney, Agent, or Firm—Oblon, Fisher, Spivak, McClelland & Maier

[57] ABSTRACT

A method treating vascular lesions or deterioration of biological membranes comprising the step of administering to a human or other mammal suspected of having one or more vascular lesions or of having deterioration of a biological membrane in the liver of said human or mammal an amount of somatostatin sufficient to reduce the number or severity of said lesions or to prevent further deterioration or reduce the extent of deterioration of said membrane.

19 Claims, No Drawings

USE OF SOMATOSTATIN IN THE PREVENTION AND CURE OF VASCULAR, MEMBRANE, OR ORGAN LESIONS

BACKGROUND OF THE INVENTION

1. Field of the Invention

This invention relates to a method of treating and preventing lesions in blood vessels and in other biological membranes, particularly in the liver, and more particularly to the use of somatostatin and its analogues to achieve these results.

2. Description of the Prior Art

Somatostatin is a peptide hormone originally investigated because of its inhibitory effects against pituitary growth hormone, which is also known as somatotropin. Somatostatin is therefore sometimes known as somatotropin release inhibiting factor (SRIF).

More recent studies have shown that pretreatment with exogenous somatostatin prevents cysteamine-induced duodenal ulcer, with minimal inhibition of gastric acid output (Schwedes et al, *Eur. J. Pharm.* 44, 195 (1977)). In addition, somatostatin has been shown to have a beneficial effect on experimentally-induced pancreatitis (Schwedes et al, *Horm. Metab. Res.,* 11, 142 (1979)), and adrenal and lung lesions, (Schwedes et al., *Metabolism Suppl.* 1, 27, 1377 (1978)). However, the mechanism of these protective effects is unclear and no general mechanism for the protective action of somatostatin is known. Specifically, it was not known prior to the present investigations that somatostatin would be of benefit in other tissues or organ systems.

Research into the protection of hepatocytes and hepatic vasculature in various disease states and in the presence of various poisons or toxins also indicates that new agents of clinical use in this area would be of great benefit in the treatment and prophylaxis of humans and other mammals.

SUMMARY OF THE INVENTION

Accordingly, it is an object of this invention to provide a method of preventing or treating blood vessel lesions caused by the presence of toxins.

It is a further object of this invention to provide a method of preventing or treating biological membrane lesions and other types of membrane destabilizations in the liver of a human or mammal exposed to an endogenous or exogenous toxin.

These and other objects of the invention as will hereinafter become more readily apparent, have been accomplished by providing a method of treating vascular lesions by administering to a human or animal suspected of having one or more vascular lesions an exogenous amount of somatostatin sufficient to reduce the number or severity of said lesions.

DESCRIPTION OF THE PREFERRED EMBODIMENTS

The structure of somatostatin has been established by analytical investigations and chemical synthesis. Somatostatin is a cyclic tetradecapeptide having the following structure:

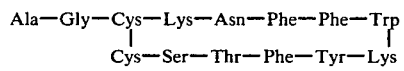

Somatostatin can be isolated from bovine hypothalamic extracts, as disclosed in Brazeau et al, *Science,* 179, 77 (1973) or can be synthesized, for example as disclosed in Rivier et al, *Compt. Rend. Ser. D,* 276, 2737 (1973); Sarantakis et al, *Biochem. Biophys. Res. Commun.,* 54, 234 (1973); Yamashiro et al, ibid., 882; and Coy et al, ibid., 1267, all of which disclosures of isolation and syntheses being hereby incorporated by reference. The synthetic linear form of the peptide shows identical biological activity to the natural cyclic or synthetic cyclic (oxidized) forms.

Somatostatin has been shown in the present studies to be an effective agent for preventing lesions of blood vessels, especially lesions of hepatic blood vessels in mammals. In addition somatostatin has been shown to be effective in preventing deterioration of biological membranes in the livers of mammals. By deterioration is meant a lesion or any state of membrane health that intervenes between a state of proper membrane health and a lesion. States that would lead to the formation of a lesion of untreated are known as pre-lesions. By lesion is meant any pathological discontinuity of tissue or loss of function of a membrane or vascular wall. Somatostatin is also expected to be effective in the treatment of preexisting lesions and membrane deterioration. Somatostatin is believed to stabilize biological membranes against the formation of new lesions or deterioration and to reduce the extent of existing lesions and membrane deterioration.

The present invention comprises administering somatostatin or its derivatives to prevent and treat hepatic and vascular lesions caused by a variety of exogenous and endogenous toxins (known collectively as chemical toxins) and other agents; in fact, for any agent which causes deterioration of cellular membranes, particularly hepatic vessels and membranes. Examples of agents that cause vascular damage and against which samatostain is expected to be effective include endogenous agents, such as vasoactive amines, and exogenous agents, such as therapeutic and diagnostic drugs like sulfa drugs, penicillin derivatives, estrogens, and chemotherapeutic agents as well as plant and animal toxins. Vascular deterioration as a result of disease, for example endotoxic shock, Gram-negative bacterial sepsis, and disseminated intravascular coagulation, should also be amenable to treatment or prevention by somatostatin.

The structure of somatostatin has been disclosed above. Derivatives and analogues of somatostatin having similar structure and biological effects are considered to be encompassed by this invention. Both cyclic and linear derivatives are permissible. Preferred is somatostatin itself, either in linear or cyclic form.

Somatostain may be used to treat any mammal, although treatment of humans is preferred. Suitable dosages of somatostatin are 1 µg to 10 mg/kg of body weight. Preferred are dosages in the range of 0.1 to 1.5 mg/kg. Most preferred is about 1.25 mg/kg. Administration may be in a single dose or may be spread out over time by administration of multiple small doses or by slow intravenous administration of a dilute solution of somatostatin. The maximum dose per day should not exceed 10 mg/kg of body weight.

The dosage may be administered by intravenous, subcutaneous or intramuscular injection or intragastrically. Administration by intravenous or subcutaneous injection is preferred. When administered in the form of an injection, any non-toxic pharmaceutical carriers may be used, provided that the carrier does not cause hydrolysis of the somatostatin peptide bonds or otherwise interfere with the action of somatostatin. Suitable carriers include water, aqueous solutions of non-toxic salts and organic compounds, and non-toxic organic solvents, such as ethanol. Preferred are isotonic aqueous solutions, such as solution of NaCl and glucose. Most preferred for subcutaneous injections are solutions containing protamine sulfate and $ZnCl_2$ (about 0.05% and about 0.13 mg/ml, respectively), as these materials prolong the activity of somatostatin, particularly when injected subcutaneously.

Somatostatin may be administered alone or concurrently with other medical materials. Preferred is administration with other materials that also alleviate the action of lesion-causing agents, such as prostaglandins.

Administration may occur after the presence of a lesion is suspected or confirmed, or under conditions in which lesions might be expected to occur, for example, during chemotherapy.

The effectiveness of somatostatin has been demonstrated in a model study using the toxin phalloidin, a toxin isolated from the poisonous mushroom *Amanita phalloides*. This toxin kills rats within about 4 hours after intraperitoneal injection. Rats injected with phalloidin show a massive increase in liver size accompanied by hemorrhage. In a control group of rats given phalloidin but no somatostatin, 22 or 24 rats died within 2-4 hours. Autopsy of these rats revealed a 70% average increase in liver weight, and light microscopy showed vacuolization of hepatocytes, congestion, and hemorrhagic necrosis. In the test group of 26 animals that were treated with both phalloidin and somatostatin, only 8 rats died. Furthermore, only a 30% average increase in liver weight was found in 10 animals treated with somatostatin and phalloidin and sacrificed four hours after intoxication. Histologic examination revealed only mild vacuolization of hepatocytes and slight congestion.

These results were confirmed in additional biochemical and morphologic experiments. In both cases, rats were given saline (control), phalloidin alone, or phalloidin and somatostatin. Somatostatin was given in subcutaneous injections in a solution of protamine sulfate and zinc chloride in order to prolong its effectiveness, or in normal saline.

In the biochemical experiments, the animals were also injected with Evans blue 15 min before autopsy. At autopsy the portal vein was perfused in situ with 20 ml of saline to remove blood from hepatic vasculature. Phalloidin caused a time dependent increase in the hepatic uptake of Evans blue, indicative of leakage of blood into the tissue through blood vessel lesions. Somatostatin treatment virtually abolished this enhanced uptake of the dye. In the morphologic experiments, groups of rats were also injected with colloidal carbon (India ink, 0.1 mg/100 g i.v.) 15 min before autopsy. At that time pieces of liver were processed for subsequent light or electron microscopic studies. Light microscopy revealed a uniform uptake of carbon particles in Kupffer cells of the liver of control animals. In rats given phalloidin, carbon labeling of sinusoidal macrophages was decreased in the centrilobular areas, while early deposits of carbon were seen along the sinusoidal walls in the periportal regions. Subsequently, these areas showed severe congestion and hemorrhage. Somatostatin pretreatment markedly decreased the differential distribution of India ink in the liver after phalloidin administration and virtually abolished the carbon labeling of sinusoidal walls. Electron microscopy confirmed the phagocytosis of carbon by Kupffer cells and showed early breakdowns in the endothelium of sinusoids in the liver of rats given phalloidin. As opposed to controls, carbon particles were also seen beyond endothelial cells and in Disse space soon after phalloidin injection. Subsequently, vacuolation of hepatocytes and increased amount of extravascular plasma-like material were noticed. These changes were markedly diminished or absent in the livers of rats given somatostatin and phalloidin. Parallel administration of the sulfhydryl blocker N-ethylmaleimide (N-EM) counteracted the beneficial effect of somatostatin suggesting that endogenous (tissue) thiols and/or sulfhydryl groups in somatostatin itself might be important for the cytoprotective or organoprotective action of somatostatin. The latter possibility was corroborated by structure-activity studies in which equimolar doses of a somatostatin analogue without thiol groups were shown to be inactive under the same test conditions.

The above disclosure generally describes the present invention. A more complete understanding can be obtained by reference to the following specific examples, which are provided herein for purposes of illustration only, and are not intended to be limiting unless otherwise specified.

EXAMPLE 1

In all of the experiments, female or male Sprague-Dawley rats (150-200 g) were used. The animals were given free access to Purina lab chow and tap water. Each group consisted of at least 3-4 rats; every experiment was repeated at least twice and the results were pooled.

Control animals were injected with normal saline 30 min prior to sacrifice and autopsy. Animals treated with phalloidin alone were injected i.p. with 0.12 mg/100 g body weight 15 min, 30 min, or 60 min before sacrifice and autopsy. Animals treated with both phalloidin and somatostatin received phalloidin as above in addition to 250 $\mu$g s.c. somatostatin at 30 and 10 minutes before the phalloidin injection. The first somatostatin injection was dissolved in 1 ml of solution consisting of 0.5 ml of 0.1% protamine sulfate and 0.5 ml of $ZnCl_2$, 250-260 $\mu$g/ml. The second somatostatin injection was given in normal saline. In addition, rats of all groups were given Evans blue, 1 mg/100 g i.v., 15 min before sacrifice and autopsy. Livers were prefused with 20 ml of saline in situ through the protal vein to remove intravascular dye prior to measuring dye uptake by the liver tissue. Evans blue does not pass through intact blood vessel walls in substantial quanity and dye uptake in the liver is thus a measure of vascular and hepatic membrane lesions and other deteriorations.

The results of these experiments are shown in Table 1. A one gram sample from the left lobe was measured spectrophotometrically to determine the uptake of Evans blue dye in $\mu$g/g liver tissue. As can be seen from the results as shown in Table 1, there is a time dependent uptake of Evans blue dye into the livers of animals treated with phalloidin. This effect is prevented or significantly decreased in the presence of somatostatin, demonstrating the preventive effects of somatostatin on lesion formation as a result of the presence of chemical toxins.

TABLE 1

Effect of phalloidin and somatostatin on hepatic concentration of Evans blue in the rat

| Group | Treatment[A] | Time (min) (after phalloidin) | Evans blue ($\mu$g/g liver)[B] |
|---|---|---|---|
| 1. | Saline | — | 8.67 ± 1.68 |
| 2. | Phalloidin | 16 min | 11.21 ± 2.40 |
| 3. | " | 30 min | 28.50 ± 4.67 |
| 4. | " | 60 min | 51.08 ± 13.56 |
| 5. | Somatostatin + Phalloidin | 16 min | 7.17 ± 0.64 |
| 6. | " | 30 min | 16.93 ± 4.76 |
| 7. | " | 60 min | 15.50 ± 4.65 |

[A]In addition, rats of all groups were given Evans blue, 1 mg/100g i.v. once, 15 min before autopsy.
[B]Livers were perfused with 20ml of saline In situ through the portal vein to remove the intravascular dye.

EXAMPLE 2

In the present studies, Sprague-Dawley rats with an initial body weight of about 200 g had free access to Purina lab chow and tap water. Each control and experimental group consisted of 3-5 animals; every experiment was performed at least twice and the results were pooled.

Somatostatin (250 $\mu$g in 1 ml of protamine sulfate and $ZnCl_2$ suspension) was injected s.c. 30 min before and 30 min after the administration of phalloidin (0.12 mg/100 g i.p.). In addition, 10 min before the toxin, another dose of 250 $\mu$g of somatostatin in 1 ml of distilled water was given i.p. Other groups of rats also received the sulfhydryl blocker N-ethylmaleimide (alone or in combination with somatostatin), 2 mg/100 g s.c. 20 min before and 40 min after phalloidin. A —SH free agalogue of somatostatin was used instead of the regular somatostatin in the same dose and at the same time in some experiments. This —SH free analogus was Di-S-tBu-Somatostatin, in which the hydrogens of the —SH groups (cystein) were replaced with t-butyl groups. Groups of rats were either sacrificed 1 hr after intoxication, or were observed for mortality (which invariably occurred within 2-4 hr) and survivors were killed in 24 hr. The hemorrhagic liver lesions were evaluated on a scale of 0-3, where 0=normal, 1=multifocal (1-5 mm) hemorrhages, 2=large hemorrhagic areas entirely involving one lobe (usually the left and-/or medium), 3=enlargement and uniform hemorrhage involving the whole liver.

This study showed (Table 2) the well-known focal or generalized hemorrhagic enlargement and necrosis of the liver found in rats given phalloidin alone as described previously. These lesions, as well as the mortality, were significantly diminished by somatostatin treatment. In contrast to this, N-ethylmaleimide counteracted the protective action of regular somatostatin, and the sulfhydryl-free derivative of somatostatin was without effect.

TABLE 2

Effect of somatostatin and N—ethylmaleimide on the toxicity of phalloidin

| Group | Pretreatment (before phalloidin) | Hepatic lesions (Scale: 0-3) | Mortality (%) |
|---|---|---|---|
| 1. | None | 2.9 ± 0.1 | 100 |
| 2. | Somatostatin | 0.7 ± 0.2 * | 20 * |
| 3. | N—Ethylmaleimide (N—EM) | 2.3 ± 0.2 | 90 |
| 4. | Somatostatin + N—EM | 2.1 ± 0.3 | 86 |
| 5. | di-S—tBu-Somatostatin | 2.7 ± 0.2 | 92 |

* = $p < 0.05$

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A method of treating hepatic vascular lesions, comprising:
   administering to a human or other mammal suspected of having one or more hepatic vascular lesions an amount of somatostatin sufficient to reduce the number or severity of said lesions.
2. The method of claim 1, wherein said lesions are caused by a chemical toxin.
3. The method of claim 1, wherein somatostatin is administered in an amount of from 0.1 to 1.5 mg/kg of body weight.
4. The method of claim 3, wherein said amount is about 1.25 mg/kg of body weight.
5. The method of claim 1, wherein said administering is by intravenous or subcutaneous injection.
6. The method of claim 1, wherein somatostatin is administered to a human.
7. A method of stabilizing hepatic tissue in vivo, comprising:
   administering to a human or other mammal suspected of having deterioration of a biological membrane in the liver of said human or mammal an amount of somatostatin sufficient to prevent further deterioration or reduce the extent of deterioration of said membrane.
8. The method of claim 7, wherein said deterioration is caused by a chemical toxin.
9. The method of claim 7, wherein said destabilization is a lesion or pre-lesion.
10. The method of claim 9, wherein said destabilization is a lesion.
11. The method of claim 7, wherein somatostatin is administered in an amount of from 0.1 to 1.5 mg/kg of body weight.
12. The method of claim 7, wherein said administering is by intravenous or subcutaneous injection.
13. The method of claim 7, wherein said administering is to a human.
14. A method of stabilizing hepatic tissue in vivo, comprising:
   administering an amount of somatostatin sufficient to prevent deterioration or reduce the extent of deterioration of a biological membrane in the liver of a human or other mammal prior to or concurrently with the administration of an agent known to cause lesions of hepatic tissue.
15. The method of claim 14, wherein said agent is a therapeutic or diagnostic drug.
16. A method of claim 14, wherein somatostatin is administered in an amount of from 0.1 to 1.5 mg/kg of body weight.
17. The method of claim 16, wherein said amount is about 1.25 mg/kg of body weight.
18. The method of claim 14, wherein said administering is by intravenous or subcutaneous injection.
19. The method of claim 14, wherein said administering is to a human.

* * * * *